United States Patent
Chilla

(10) Patent No.: US 8,877,295 B2
(45) Date of Patent: Nov. 4, 2014

(54) PROCESS FOR THE PRODUCTION OF MULTI-LAYER COATINGS

(75) Inventor: Marc Chilla, Sprockhoevel (DE)

(73) Assignee: Axalta Coating Systems IP Co., LLC, Wilmington, DE (US)

( * ) Notice: Subject to any disclaimer, the term of this patent is extended or adjusted under 35 U.S.C. 154(b) by 784 days.

(21) Appl. No.: 12/644,775

(22) Filed: Dec. 22, 2009

(65) Prior Publication Data

US 2010/0159146 A1 Jun. 24, 2010

Related U.S. Application Data

(60) Provisional application No. 61/203,557, filed on Dec. 23, 2008.

(51) Int. Cl.
| | |
|---|---|
| *B05D 7/16* | (2006.01) |
| *B05D 7/00* | (2006.01) |
| *B05D 7/14* | (2006.01) |
| *C09D 5/02* | (2006.01) |
| *C12N 15/10* | (2006.01) |

(52) U.S. Cl.
CPC ........ *C12N 15/1013* (2013.01); *B05D 2202/00* (2013.01); *B05D 2201/00* (2013.01); *B05D 7/572* (2013.01); *B05D 7/14* (2013.01); *C09D 5/028* (2013.01)

USPC .................................................. 427/407.1

(58) Field of Classification Search
USPC .................................................. 427/407.1
See application file for complete search history.

(56) References Cited

U.S. PATENT DOCUMENTS

| | | | | |
|---|---|---|---|---|
| 5,976,343 | A | * | 11/1999 | Schlaak .................... 205/198 |
| 2006/0008588 | A1 | | 1/2006 | Chilla et al. |
| 2006/0068116 | A1 | | 3/2006 | Chilla et al. |
| 2006/0134334 | A1 | | 6/2006 | Chilla et al. |

FOREIGN PATENT DOCUMENTS

| | | |
|---|---|---|
| WO | 2007041228 A | 4/2007 |
| WO | 2007146386 A | 12/2007 |
| WO | 2008051346 A1 | 5/2008 |

OTHER PUBLICATIONS

European Search Report for EP App. No. 09177931, mailed on Mar. 10, 2010.

* cited by examiner

*Primary Examiner* — William Phillip Fletcher, III

(74) *Attorney, Agent, or Firm* — Ingrassia Fisher & Lorenz, P.C.

(57) ABSTRACT

A process for the production of base coat/clear coat multi-layer coatings in an A' color shade wherein the base coat layer is applied in a first layer from a water-borne base coat AB and in a second layer from a water-borne base coat A with low hiding power and having a color shade A', wherein the water-borne base coat AB is a mixture of the water-borne base coat A and a water-borne base coat B with sufficient hiding power.

9 Claims, No Drawings

PROCESS FOR THE PRODUCTION OF MULTI-LAYER COATINGS

CROSS-REFERENCE TO RELATED APPLICATION

This application claims priority under 35 U.S.C. §119 from U.S. Provisional Application Ser. No. 61/203,557, filed Dec. 23, 2008, which is hereby incorporated by reference in its entirety.

FIELD OF THE INVENTION

The invention relates to a process for the production of multi-layer coatings.

BACKGROUND OF THE INVENTION

Automotive coatings generally comprise an electrodeposition coating (EDC) primer, a primer surfacer layer (filler coating layer) applied thereto and a top coat applied thereto comprising a wet-on-wet applied color- and/or special effect-imparting base coat layer and a protective, gloss-imparting clear coat layer. During automotive body OEM coating (automotive body original coating; OEM=original equipment manufacture), such multi-layer coatings are conventionally very largely automatically applied in industrial coating facilities, wherein at least on application of the base coat a number of differently colored base coats corresponding to the color shade program is processed. In some coating facilities, even the primer surfacer is here applied using two or more primer surfacers in each case of a different color shade. One or more of the base coats used is/are here assigned to each individual primer surfacer while taking account of the color shades in question; i.e., the attempt is made to ensure the greatest possible similarity in color shade between the color shade of the primer surfacer and that of the base coat. The aim here is to ensure that any stone chip damage accompanied by detachment of the base coat which occurs during use of the motor vehicle remains as visually unobtrusive as possible.

Automotive plastics coatings generally comprise an electrically conductive plastics primer and a top coat applied thereto comprising a wet-on-wet applied color- and/or special effect-imparting base coat layer and a protective, gloss-imparting clear coat layer, although, dependent on the plastics type and its pretreatment, it may also be possible to omit the plastics primer. As described in the preceding paragraph for the automotive body OEM coating, the original coating of automotive plastics parts is conventionally performed very largely automatically in industrial coating facilities, wherein in this case too at least on application of the base coat a number of differently colored base coats corresponding to the color shade program is processed. Here, in some coating facilities two or more plastics primers each of a different color shade are used. Similarly, two or more plastics parts for primerless coating (plastics parts to be coated primerless; plastics parts not to be coated with primer) and which each differ in plastics material color may be used. As described in connection with primer surfacer coating, the base coats are also assigned on the basis of color shade in the case of differently colored plastics primers or differently colored plastics parts for primerless coating.

There are, however, also industrial coating facilities in which the effort of tailoring the colors of primer surfacer and base coat or of plastics primer or plastics parts for primerless coating and base coats to one another is avoided. For example, for reasons of rationalization, just one primer surfacer or just one plastics primer or plastics parts for primerless coating of only one color are used here. The primer surfacer, plastics primer or plastics parts for primerless coating are here generally of a color shade which is a compromise (compromise color shade). Such a compromise color shade is usually a shade of grey. In the case of base coats with elevated hiding power, this causes no problems with regard to color shade feasibility (achievability of the nominal color shade). However, depending on the compromise color shade and the base coat color shade, color shade feasibility problems may occur in the case of base coats with low hiding power. For example, such a base coat with a problematic color shade must be applied in a very high film thickness to achieve color shade consistency. Color shade consistency or achieving color shade consistency here means that a visually imperceptible color shade deviation $\Delta E$ from the color shade of a coating layer applied from the base coat in question in a black/white opaque or even greater film thickness is ensured. In the case of solid color shades, $\Delta E$ values of <0.4 determined at an illumination angle of 45° to the perpendicular and an observation angle of 45° relative to the specular reflection are sufficiently small and thus represent color shade consistency in the above sense. In the case of special effect color shades (color shades dependent on observation angle; pigment content comprises at least one special effect-imparting pigment) $\Delta E$ values are sufficiently small if they, when determined at an illumination angle of 45° to the perpendicular and at observation angles of 15, 25, 45, 75 and 110° relative to the specular reflection, are in each case <1.

The elevated base coat film thickness required to achieve color shade consistency not only entails high base coat consumption which is undesirable from both an environmental and an economic standpoint, but may also entail disadvantages for the technological properties of the multi-layer coating or may simply mean non-compliance with the specified nominal base coat film thickness.

By the way, it is not possible to achieve any base coat film thickness in automatically-operated industrial coating lines. The latter are operated in work cycles, i.e. only a limited period of time is available for the coating of each single substrate. The work cycle time, number and type of spray equipment and the area to be coated determine the maximum base coat film thickness that can be achieved with a given water-borne base coat. In state-of-the-art automatically-operated industrial coating lines the maximum film thickness that can be achieved with conventional water-borne base coats is in the range of 20 to 30 µm. Higher base coat film thicknesses can only be achieved by increasing the number of work cycles per substrate which means loss in productivity.

One theoretical approach would also be to adjust the pigment/binder ratio in the base coat in favor of the pigment content and in this way to counteract an elevated base coat film thickness. From a practical standpoint, however, this is not a suitable solution, because multi-layer coatings produced with such highly pigmented base coats exhibit technological weaknesses, in particular with regard to adhesion and stone chip resistance. Moreover, optical appearance is impaired, this being visually perceptible as texture and matting and instrumentally detectable as lower distinctness of image (DOI).

WO 2008/051346 discloses a method for producing primer surfacer-free multi-layer coatings consisting of an electrodeposition coating layer, a first water-borne base coat layer, a second water-borne base coat layer and a clear coat layer on metal substrates. The second water-borne base coat layer is here applied in a comparatively low film thickness from an unmodified water-borne base coat with low hiding power, while the first water-borne base coat layer is applied from a modified water-borne base coat. The modified water-borne base coat is a mixture of the unmodified water-borne base coat, a further water-borne base coat which is likewise unmodified but has sufficient hiding power and a pigment-free admixture component providing polyisocyanate or binder.

SUMMARY OF THE INVENTION

The invention is directed to a process for the production of multi-layer coatings in an A' color shade on substrates, comprising the successive steps:
1) applying a base coat layer in a total process film thickness in the range from 8 to 20 µm to substrates selected from the group consisting of metal substrates provided with a pre-coating comprising an external primer surfacer layer, plastics substrates provided with a plastics primer precoating and uncoated plastics substrates,
2) applying a clear coat layer onto the base coat layer,
3) jointly curing the base coat and clear coat layers,
wherein the base coat layer is applied in a first layer and in a second layer; the first layer comprises a water-borne base coat AB and the second layer comprises a water-borne base coat A having a color shade A',
wherein the water-borne base coat A has low hiding power,
wherein the water-borne base coat AB is a mixture of 100 pbv (parts by volume) of the water-borne base coat A and 1 to 400 pbv, for example, 1 to 50 pbv of a water-borne base coat B having a color shade B', and
wherein the pigment content of the water-borne base coat B is made such that the multi-layer coatings achieved after step 3) achieve color shade consistency from in each case at least 80% (from in each case 80% and upwards, as far as it makes technical sense) of the individual process film thickness both of the layer applied from the water-borne base coat AB and of the layer applied from the water-borne base coat A.

DETAILED DESCRIPTION OF THE EMBODIMENTS

The film thicknesses indicated in the description and in the claims for coating layers refer in each case to dry film thicknesses. In the description and the claims the term "process film thickness" is used. The meaning of this term will be explained hereinbelow.

The term "black/white opaque" or "black/white opacity" is used in the description and the claims. It refers to the dry coating thickness of a coating composition wherein the contrast between the black and white fields of a black and white chart coated with the coating composition is no longer visually discernible (mean coating thickness value determined on the basis of evaluation by 5 independent individuals). Following ISO 6504-3:2006 (E), method B, in order to determine this coating thickness, the coating composition of which the black/white opacity is to be investigated may be applied in a wedge shape onto a black and white chart and dried or hardened.

The term "pigment content" used in the description and in the claims means the sum of all the pigments contained in a coating composition without fillers (extenders). The term "pigments" is used here as in DIN 55944 and covers, in addition to special effect pigments, inorganic white, colored and black pigments and organic colored and black pigments. At the same time, therefore, DIN 55944 distinguishes between pigments and fillers.

The phrase used in the description and the claims "color shade consistency of the multi-layer coatings from in each case at least 80% of the individual process film thickness both of the layer applied from the water-borne base coat AB and of the layer applied from the water-borne base coat A" means that the color difference $\Delta E$ [$\Delta E$ can be determined by goniospectrophotometric colorimetry and it equals the square root of $(\Delta L^{*2}+\Delta C^{*2}+\Delta h^{*2})$; $L^*$, $C^*$, $h^*$=lightness, chroma, hue] between multi-layer coatings to be compared and applied from water-borne base coat AB, water-borne base coat A and clear coat is sufficiently small if the base coat layers applied both from the water-borne base coat AB and from the water-borne base coat A have each been applied to 80% or more of the individual process film thickness. In the case of solid color shades, $\Delta E$ values of <0.4 determined at an illumination angle of 45° to the perpendicular and an observation angle of 45° relative to the specular reflection are sufficiently small and thus represent color shade consistency in the above sense. In the case of special effect color shades (dependent on observation angle; pigment content comprises at least one special effect-imparting pigment) $\Delta E$ values are sufficiently small if they, when determined at an illumination angle of 45° to the perpendicular and at observation angles of 15, 25, 45, 75 and 110° relative to the specular reflection, are in each case <1.

In goniospectrophotometric colorimetry the reflectance curves of visible light in the range from, for example, 380 to 800 nm of a coated surface are determined at one or more different observation angles. The reflectance curves may, for example, be determined at 5 observation angles, for example at 15, 25, 45, 75 and 110° relative to the specular reflection. The reflectance curves may be used as the basis for calculating the conventional CIELab system colorimetric parameters $L^*$ (lightness), $a^*$ (red-green value), $b^*$ (yellow-blue value) and further also $C^*$ (chroma) and $h^*$ (hue) (c.f. DIN 6174) or these values are directly output from the measuring instrument. The reflectance curves may be determined using any conventional colorimeters known to the person skilled in the art, for example, the X-Rite MA 68 II instrument sold by the company X-Rite.

In the process according to the invention substrates selected from the group consisting of metal substrates provided with a precoating comprising an external primer surfacer layer, plastics substrates provided with a plastics primer precoating and uncoated plastics substrates are provided with a multi-layer coating in an A' color shade.

The metal substrates are in particular automotive bodies or automotive body parts. The metal substrates may comprise a conventional pretreatment, for example phosphating and optionally additionally passivation. The precoating comprising an outer primer surfacer layer may consist of a primer surfacer layer which has been applied directly onto the metal substrate surface and cured, but in general it will also comprise at least one coating layer located beneath the external primer surfacer layer, for example an electrodeposition primer layer or an electrodeposition primer and a stone chip protection layer. The primer surfacer, stone chip protection and electrodeposition coating layers or the coating compositions used for the production thereof are coating compositions and layers which are conventional in the field of automotive body OEM coating and known to a person skilled in the art. The production of metal substrates provided with such coatings is also known to a person skilled in the art.

The plastics substrates comprise in particular automotive plastics parts or automotive plastics attachments such as, for example, bumpers, collision protection strips, side trim, sills, mirror housings, door handles, bonnets, boot lids, hatchbacks, wings, spoilers and hubcaps. As stated, the plastics substrates may be uncoated or precoated with a plastics primer layer. Plastics primers are coating layers or coating compositions which are conventional in the field of plastics coating and known to a person skilled in the art. The production of plastics substrates provided with a precoating of plastics primer is also known to a person skilled in the art. The function of the plastics primers resides for example in an adhesion-promoting action towards coating layers which are subsequently to be applied. Plastics primers may be formulated to be electrically conductive by a content of appropriate constituents and in this manner serve as conductive primers which enable or facilitate electrostatic overcoatability with further coating compositions.

The process according to the invention makes it possible, irrespective of the color shade of the substrates to be coated, to produce multi-layer coated substrates in a color shade A' without having to apply the corresponding water-borne base coat A with low hiding power in an elevated film thickness.

In a particular embodiment, the process according to the invention makes particularly full use of its advantages. This is the case, if at least some of the substrates to be coated in step 1), preferably all the substrates to be coated in step 1) (i.e. their primer surfacer layer, their plastics primer layer or the uncoated plastics substrates themselves) have color shades which, even when overcoated with a 20 μm thick layer of a water-borne base coat A in question, do not allow color shade consistency to be achieved. The process according to the invention is in particular advantageous, if all the substrates to be coated in step 1) have one and the same color shade or compromise color shade which, even when overcoated with a 20 μm thick layer of a water-borne base coat A in question, does not allow color shade consistency to be achieved.

In step 1) of the process according to the invention, the substrates are provided with a base coat layer in a total process film thickness in the range from 8 to 20 μm. This base coat layer is applied in two layers, i.e., a first layer having an individual process film thickness in the range from 50 to 80% of the total process film thickness, for example, in the range from 6 to 15 μm of a water-borne base coat AB is applied and a subsequent second layer in an individual process film thickness in the range from 20 to 50% of the total process film thickness, for example, in the range from 2 to 10 μm of the water-borne base coat A then is applied. The total process film thickness of the base coat layer is dependent inter alia on color shade. Car manufacturers' requirements for base coat film thickness are expressed in the so-called process film thickness (average film thickness which is desired over the entire body in the automotive body OEM coating process), which depends on the individual color shade, on technological properties to be achieved (e.g., stone chip resistance) and on an economic application of the relevant water-borne base coat, i.e., in as thin a film as possible. The total base coat process film thickness lies in the range from 8 to 20 μm and is the sum of, for example, 6 to 15 μm of the water-borne base coat AB plus, for example, 2 to 10 μm of the water-borne base coat A. Such film thicknesses for base coats meet the requirements for coating the relevant substrates, for example, automotive bodies. In particular, this means that a specific value within this range from 8 to 20 μm represents the specific total process film thickness for a particular base coat, for example, a base coat of a particular color shade. Said specific total process film thickness is here composed of the sum of the specific individual process film thickness, lying within the range of, for example, 6 to 15 μm, of the corresponding water-borne base coat AB and the specific individual process film thickness, lying within the range of, for example, 2 to 10 μm of the corresponding water-borne base coat A.

In the present invention a distinction is drawn between water-borne base coats A, B and AB. Whereas the water-borne base coats A are water-borne base coats with problematic color shades and having low hiding power, the water-borne base coats B are water-borne base coats with unproblematic color shades and having sufficient hiding power.

The color shades of a coating applied from a water-borne base coat A in at least black/white opaque film thickness (with or without clear top coat) and of a corresponding multi-layer coating prepared according to the process of the invention are so close to each other that an observer virtually cannot perceive a difference between the color shades, i.e. the color shade of the corresponding multi-layer coating prepared according to the process of the invention reaches color shade consistency with the color shade of the coating applied from the water-borne base coat A in at least black/white opaque film thickness (with or without clear top coat). Therefore, in the present description and the claims, the color shades of the water-borne base coats A and of coatings applied thereof in at least black/white opaque film thickness (with or without clear top coat) are called color shades A'. The color shades of the corresponding multi-layer coatings prepared according to the process of the invention are also called color shades A'. Accordingly, the color shades of the water-borne base coats B and of coatings applied thereof in black/white opaque film thickness (with or without clear top coat) are called color shades B'.

The water-borne base coats AB may be produced by mixing 100 pbv of water-borne base coat A with 1 to 400 pbv, for example, 1 to 50 pbv of a water-borne base coat B. The water-borne base coat B to be mixed with the water-borne base coat A may be one individual water-borne base coat B or a mixture of two or more different water-borne base coats of the B type; preferably it is one individual water-borne base coat B. Usually the mixing ratio will be 100 pbv of water-borne base coat A:1 to 50 pbv of water-borne base coat B. A mixing ratio of 100 pbv of water-borne base coat A:more than 50 to 400 pbv of water-borne base coat B applies in particular in case the water-borne base coat B is a light-colored or even a white water-borne base coat.

The water-borne base coats A and B must be chemically compatible with each other, i.e. miscible with each other without problems, for example, without formation of coagulate or precipitate. Whereas this is generally guaranteed in case water-borne base coats A and B are supplied by the same paint manufacturer, it is necessary to ensure such compatibility in case there is more than one supplier for the water-borne base coats A and B. The water-borne base coats A and B to be mixed should not differ from each other too much in viscosity to allow for easy mixing. For example, the difference in viscosity should not exceed 50 mPa·s at a shear rate of 1000 $s^{-1}$ at 20° C.

The water-borne base coats A, B and AB are aqueous coating compositions having a ratio by weight of pigment content to resin solids content of, for example, 0.05:1 to 1:1. In addition to water, pigment(s), a resin solids content, which comprises binder(s), optionally, paste resin(s) and optionally, cross-linking agent(s), optionally, filler(s) and optionally, organic solvent(s), the water-borne base coats A, B and AB contain in general also conventional additive(s).

The water-borne base coats A, B and AB contain ionically and/or non-ionically stabilized binder systems. In case of ionic stabilization anionic stabilization is preferred. Anionic stabilization is preferably achieved by at least partially neutralized carboxyl groups in the binder, while non-ionic stabilization is preferably achieved by lateral or terminal polyethylene oxide units in the binder. The water-borne base coats A, B and AB may be physically drying or crosslinkable by formation of covalent bonds. The crosslinkable water-borne base coats A, B and AB forming covalent bonds may be self- or externally crosslinkable systems.

The water-borne base coats A, B and AB contain one or more conventional film-forming binders. They may optionally also contain crosslinking agents if the binders are not self-crosslinkable or physically drying. Examples of film-forming binders, which may be used, are conventional polyester, polyurethane, (meth)acrylic copolymer and/or hybrid resins derived from these classes of resin. Selection of the optionally contained crosslinking agents depends, in a manner familiar to the person skilled in the art, on the functionality of the binders, i.e., the crosslinking agents are selected in such a way that they exhibit a reactive functionality complementary to the functionality of the binders. Examples of such complementary functionalities between binder and crosslinking agent are: carboxyl/epoxy, hydroxyl/methylol ether and/or methylol (methylol ether and/or methylol preferably, as crosslinkable groups of aminoplast resins, in particular, melamine resins).

The term "polyurethane resin" as used in the present invention does not rule out that the polyurethane resin in question may also contain groups other than urethane groups in the polymer backbone, such as, in particular, ester groups and/or urea groups. Instead, the term "polyurethane resin" of course, also in particular, includes polyurethane resins which contain polyester polyol building blocks and/or urea groups, wherein the latter may, for example, be formed by the reaction of isocyanate groups with water and/or polyamine.

The water-borne base coats A, B and AB contain conventional pigments, for example, special effect pigments and/or pigments selected from among white, colored and black pigments.

Examples of special effect pigments are conventional pigments which impart to a coating color flop and/or lightness flop dependent on the observation angle, such as, non-leafing metal pigments, for example, of aluminum, copper or other metals, interference pigments, such as, for example, metal oxide-coated metal pigments, for example, iron oxide-coated aluminum, coated mica, such as, for example, titanium dioxide-coated mica, graphite effect-imparting pigments, iron oxide in flake form, liquid crystal pigments, coated aluminum oxide pigments, coated silicon dioxide pigments.

Examples of white, colored and black pigments are the conventional inorganic or organic pigments known to the person skilled in the art, such as, for example, titanium dioxide, iron oxide pigments, carbon black, azo pigments, phthalocyanine pigments, quinacridone pigments, pyrrolopyrrole pigments, perylene pigments.

The water-borne base coats A, B and AB may also contain fillers (extenders), for example, in proportions of 0 to 30 wt. % relative to the resin solids content. The fillers do not constitute part of the pigment content of the water-borne base coats A, B and AB. Examples are barium sulfate, kaolin, talcum, silicon dioxide, layered silicates and any mixtures thereof.

The special effect pigments are generally initially introduced in the form of a conventional commercial aqueous or non-aqueous paste, optionally, combined with preferably water-dilutable organic solvents and additives and then mixed with aqueous binder. Pulverulent special-effect pigments may first be processed with preferably water-dilutable organic solvents and additives to yield a paste.

White, colored and black pigments and/or fillers may, for example, be ground in a proportion of the aqueous binder. Grinding may preferably also take place in a special aqueous paste resin. Grinding may be performed in conventional assemblies known to the person skilled in the art. The formulation is then completed with the remaining proportion of the aqueous binder or of the aqueous paste resin.

The water-borne base coats A, B and AB may contain conventional additives in conventional quantities, for example, of 0.1 to 5 wt. %, relative to the solids content thereof. Examples are antifoaming agents, wetting agents, adhesion promoters, catalysts, leveling agents, anticratering agents, thickeners and light stabilizers.

The water content of the water-borne base coats A, B and AB is, for example, 60 to 90 wt. %.

The water-borne base coats A, B and AB may contain conventional organic solvents, for example, in a proportion of preferably less than 20 wt. %, particularly preferably, less than 15 wt. %. Examples of such solvents are mono- or polyhydric alcohols, for example, propanol, butanol, hexanol; glycol ethers or esters, for example, diethylene glycol di-C1-C6-alkyl ether, dipropylene glycol di-C1-C6-alkyl ether, ethoxypropanol, ethylene glycol monobutyl ether; glycols, for example, ethylene glycol and/or propylene glycol, and the di- or trimers thereof; N-alkylpyrrolidone, such as, for example, N-methylpyrrolidone; ketones, such as, methyl ethyl ketone, acetone, cyclohexanone; aromatic or aliphatic hydrocarbons, for example, toluene, xylene or linear or branched aliphatic C6-C12 hydrocarbons.

The water-borne base coats A, B and AB have solids contents of, for example, 10 to 40 wt. %, preferably, of 15 to 30 wt. %.

The water-borne base coats A are water-borne base coats with problematic color shades and having low hiding power. The water-borne base coats A should here not be confused with deliberately transparent water-borne base coats which have virtually no hiding power. In a first embodiment, the water-borne base coats A are solid color base coats, then they have a black/white opacity of, for example, >25 μm, for example in the range of >25 μm to 80 μm. In a second embodiment, the water-borne base coats A are special effect base coats, then they have a black/white opacity of, for example, >15 μm, for example in the range of >15 μm to 80 μm.

The water-borne base coats A comprise pigments which according to the kind and/or quantity thereof allow only for a low hiding power. Examples are in particular water-borne base coats A with certain, in particular luminous blue, red, yellow or orange color shades which are especially distinguished by elevated brilliance and color purity. As already mentioned, they may comprise solid color shades or special effect color shades, such as mica or metallic color shades.

Depending on the (compromise) color shade of a substrate to be coated, the water-borne base coats of type A may include representatives which, when applied in a film thickness of 20 μm onto the substrate in question, would allow color shade consistency to be achieved. As already stated, the process according to the invention is used in the OEM multi-layer coating of substrates on an industrial scale. The substrates are here coated in a number of different color shades which constitute their color shade program, each color shade being represented by an individual water-borne base coat A. In this respect, the group of water-borne base coats A used in the process according to the invention, depending on the color shade of a substrate to be coated, may include representatives which, when applied onto the substrate in question in a film thickness of 20 μm, would allow color shade consistency to be achieved. However, the group of water-borne base coats A used in the process according to the invention may, in particular, also comprise only such representatives which, when applied in a film thickness of 20 μm onto the substrate in question, do not allow color shade consistency to be achieved.

The water-borne base coats B are water-borne base coats with unproblematic color shades and having sufficient hiding power. In a first embodiment, the water-borne base coats B are solid color base coats, then they have a black/white opacity of, for example, ≤25 μm, for example in the range of 5 to ≤25 μm. In a second embodiment, the water-borne base coats B are special effect base coats, then they have a black/white opacity of, for example ≤15 μm, for example in the range of 5 to ≤15 μm.

The water-borne base coats B comprise pigments which according to the kind and/or quantity thereof allow for sufficient hiding power. Examples are in particular water-borne base coats B with certain, in particular white, black, dark blue or green color shades. As already mentioned, they may comprise solid color shades or special effect color shades, such as mica or metallic color shades. In case they are to be mixed with a water-borne base coat A with a solid color shade, water-borne base coats B with a solid color shade are preferably used for that purpose.

The pigment content of the water-borne base coat B is made such that, with a given (particular) water-borne base coat A, a given specific total process film thickness (and in each case also specific individual process film thicknesses for the water-borne base coat AB and for the water-borne base coat A), a given mixing ratio of water-borne base coat A and B in the corresponding aforementioned range, the multi-layer coating produced from the water-borne base coat AB applied to at least 80% of the specific individual process film thickness, from the corresponding water-borne base coat A applied to at least 80% of the specific individual process film thickness and the clear coat achieves color shade consistency. In particular, the pigment content of the water-borne base coat B is selected by type (qualitative and quantitative composition of the pigments forming the pigment content) and quantity accordingly.

The pigment contents of water-borne base coats B in particular comprise hiding power imparting pigments. Pigments capable of providing hiding power are known to the skilled person developing color shades of coatings. Suitable pigment contents are, for example, those with elevated proportions of hiding power imparting pigments within the pigment composition, for example, with 30 or more wt. % of carbon black, 70 or more wt. % of titanium dioxide or 40 or more wt. % of phthalocyanine pigments.

As already mentioned, in the process according to the invention, the substrates are provided with multi-layer coatings in an A' color shade. Typically, the multi-layer coating process according to the invention is performed in an industrial coating facility, i.e. within a mass-production coating line. Generally, there are not only substrates to be provided with multi-layer coatings in A' color shades but also substrates to be provided with multi-layer coatings in B' color shades. Coating of the latter substrates is performed making use of water-borne base coats B and, in that case the water-borne base coats A and the water-borne base coats B together represent the color shade program selected for the substrates to be multi-layer coated. It is advantageous that the water-borne base coats B to be mixed with the water-borne base coats A can then be taken from the group of water-borne base coats B which represent the B' color shade program. In general the B' color shade program comprises two or more differently colored water-borne base coats B. In general, such a B' color shade program includes at least one water-borne base coat B with a white color shade, at least one water-borne base coat B with a black color shade and in general also further water-borne base coats of type B with chromatic color shades. This allows for the selection of a water-borne base coat B (one individual water-borne base coat B or a mixture of two or more different water-borne base coats B) appropriate for mixing with a relevant water-borne base coat A. In particular such selection may happen dependent on the color shade of the relevant water-borne base coat A to be mixed with. For example, a person skilled in the art will here consider the following general selection rules: if the water-borne base coat A has a light color shade, he/she will generally select a water-borne base coat B to be mixed therewith which has a likewise light, maximally similar color shade. If the water-borne base coat A has a dark color shade, he/she will generally select a water-borne base coat B to be mixed therewith which has a likewise dark, maximally similar color shade.

As already mentioned, the water-borne base coats B comprise water-borne base coats with unproblematic color shades and having sufficient hiding power. Therefore, the process for the production of multi-layer coatings on substrates in B' color shades is different from the process according to the invention. Preferably, the process for the production of multi-layer coatings in a B' color shade comprises the successive steps:

1) applying a base coat layer in a total process film thickness in the range from 8 to 20 μm from a water-borne base coat B to substrates selected from the group consisting of metal substrates provided with a precoating comprising an external primer surfacer layer, plastics substrates provided with a plastics primer precoating and uncoated plastics substrates,
2) applying a clear coat layer onto the base coat layer, and
3) jointly curing the base coat and clear coat layers.

The water-borne base coats A and B may be mixed to form water-borne base coats AB on the paint manufacturer's premises. However, the water-borne base coats A and B are mixed preferably on the user's premises (the premises of the person practicing the process according to the invention), in particular shortly or immediately before application of the resultant water-borne base coat AB.

In the case of industrial coating facilities, the water-borne base coats A and B in each case of a different color shade are each conveyed in their own circulating line. In the preferred case of mixing water-borne base coats A and B on the user's premises such mixing takes place automatically and using mixing technology conventional in industrial coating facilities, for example, a static mixer like a Kenics mixer. When applying water-borne base coat in a color shade program of n A' and m B' color shades, it is therefore not necessary to provide 2n+m circulating lines (in each case n circulating lines for the different colors of water-borne base coats A and for the different colors of water-borne base coats AB and in each case m circulating lines for the different colors of water-borne base coats B), but rather just n circulating lines for the different colors of water-borne base coats A plus m circulating lines for the different colors of water-borne base coats B.

In step 1) of the process according to the invention, the substrates are initially spray-coated with the water-borne base coat AB, preferably by electrostatically-assisted high-speed rotary atomization.

Then, preferably after a brief flash-off phase of, for example, 30 seconds to 5 minutes at an air temperature of 20 to 25° C., the corresponding water-borne base coat A is spray-applied, for example, by pneumatic spray application or by electrostatically-assisted high-speed rotary atomization.

This is preferably also followed by a brief flash-off phase of, for example, 30 seconds to 10 minutes at an air temperature of 20 to 100° C., after which the clear coat is applied in step 2) in a dry film thickness of, for example, 20 to 60 μm.

All known clear coats are in principle suitable as the clear coat. Usable clear coats are both solvent-containing one-component (1 pack) or two-component (2 pack) clear coats, water-dilutable 1 pack or 2 pack clear coats, powder clear coats or aqueous powder clear coat slurries.

After an optional flash-off phase, the applied water-borne base coat layer consisting of water-borne base coat AB and water-borne base coat A and the clear coat layer are jointly cured in step 3), for example, by baking, for example, at 80 to 160° C. object temperature.

It is advantageous that repair coating of multi-layer coatings produced by the process according to the invention can be carried out with the water-borne base coat A of the relevant problematic color shade without there being any visually perceptible deviation in color shade in the area of the repair. In other words, consistency in color shade of the kind already mentioned above is ensured, even if the repair coating is performed using only the corresponding water-borne base coat A and not also the water-borne base coat AB.

EXAMPLES

Example 1

Production of Water-Borne Base Coats a) A white water-borne base coat of the following composition was produced:

17.2 pbw (parts by weight) of resin solids (7.8 pbw of a polyester acrylate resin, 5.9 pbw of a polyurethane resin, 3.5 pbw of hexamethoxymethylmelamine)

25.1 pbw of titanium dioxide (TiPure® R 706 from DuPont)

0.2 pbw of dimethylethanol amine 0.6 pbw of polyacrylic acid thickener 0.2 pbw of defoamer 1.0 pbw polypropylene glycol 900

45.1 pbw of deionized water 10.6 pbw of organic solvents (6.6 pbw of ethylene glycol monobutyl ether, 3.1 pbw of diethylene glycol monobutyl ether, 0.9 pbw of n-propanol).

The white water-borne base coat had a black/white opacity of 22 μm.

b) A yellow water-borne base coat of the following composition was produced:

18.0 pbw of resin solids (8.1 pbw of a polyester acrylate resin, 6.2 pbw of a polyurethane resin, 3.7 pbw of hexamethoxymethylmelamine)

0.4 pbw of Irgazin® Yellow 2RLT from Ciba 2.9 pbw of titanium dioxide (TiPure® R 706 from DuPont)

5.0 pbw of Irgacolor® Yellow 3GLM from Ciba 4.2 pbw of Heucodur Yellow 3R from Heubach 0.3 pbw of dimethylethanolamine 0.2 pbw of defoamer 0.6 pbw of polyacrylic acid thickener 1.0 pbw of polypropylene glycol 900

14.6 pbw of organic solvents (4.2 pbw of ethylene glycol monobutyl ether, 1.7 pbw of diethylene glycol monobutyl ether, 0.7 pbw of ethylene glycol monohexyl ether, 3.0 pbw of N-methylpyrrolidone, 3.5 pbw of n-butanol, 1.0 pbw of n-propanol, 0.5 pbw of Shellsol T)

52.8 pbw of deionized water.

The yellow water-borne base coat had a black/white opacity of 52 μm.

c) A water-borne base coat was produced by mixing 100 pbw of the yellow water-borne base coat from b) with 400 pbw of the white water-borne base coat from a).

Example 2

Production of Multi-Layer Coatings a) A multi-layer coating was obtained by the following procedure:

The water-borne base coat 1c) was spray applied in a dry film thickness of 11 μm to automotive steel test panels 300 mm×600 mm in size and provided with an EDC primer and a dark-grey primer surfacer (lightness L*=14.6; colorimetrically determined at an illumination angle of 45° to the perpendicular and an observation angle of 45° relative to the specular reflection).

After flashing-off for 2 minutes at room temperature the yellow water-borne base coat 1b) was spray applied in a wedge-shaped gradient (wedge in longitudinal direction) to a dry film thickness range from 0 to 20 μm and allowed to flash-off for 5 minutes at 80° C.

The test panels provided in this way with a flashed off base coat layer were then spray coated with a commercial two-component polyurethane clear coat in a dry film thickness of 40 μm and after flashing-off for 5 minutes at 20° C. baked for 20 minutes at 140° C. object temperature.

b): A multi-layer coating was produced by repeating Example 2a) with the difference that the water-borne base coat 1b) was used instead of the water-borne base coat 1c), i.e., water-borne base coat 1b) was used to apply the first 11 μm thick layer as well as the wedge-shaped layer.

c): A multi-layer coating was produced without making use of water-borne base coat 1c). To this end the yellow water-borne base coat 1b) was spray applied in a dry film thickness of 60 μm to an automotive steel test panel provided with the EDC primer and the dark-grey primer surfacer. To this end 3 spray passes in each case followed by a forced drying step of 5 minutes at 70° C. were performed. Thereafter the two-component polyurethane clear coat was spray applied in a dry film thickness of 40 μm and after flashing-off for 5 minutes at 20° C. baked for 20 minutes at 140° C. object temperature.

The multi-layer coatings 2a) and 2b) so obtained were in each case colorimetrically assessed at an illumination angle of 45° to the perpendicular and an observation angle of 45° relative to the specular reflection in accordance with the method known from U.S. Pat. No. 5,991,042 using the X-Rite MA 68 II instrument sold by the company X-Rite. Multi-layer coating 2c) was colorimetrically measured using the same equipment.

Table 1 shows the ΔE values calculated from the colorimetric data as a function of the dry film thickness of the base coat layer applied as a wedge from water-borne base coat 1b) [$\Delta E_{2a}$=square root of $(L^{*}_{2c}{}^2 - L^{*}_{2a}{}^2 + c^{*}_{2c}{}^2 - c^{*}_{2a}{}^2 + h^{*}_{2c}{}^2 - h^{*}_{2a}{}^2)$; $\Delta E_{2b}$=square root of $(L^{*}_{2c}{}^2 - L^{*}_{2b}{}^2 + c^{*}_{2c}{}^2 - c^{*}_{2b}{}^2 + h^{*}_{2c}{}^2 - h^{*}_{2b}{}^2)$].

TABLE 1

| | Dry film thickness of wedge-shaped 1b)-layer (μm) | | | | | | | | | | |
|---|---|---|---|---|---|---|---|---|---|---|---|
| | 0 | 2 | 4 | 5 | 6 | 7 | 8 | 9 | 10 | 12 | 14 |
| $\Delta E_{2a}$ | 3.72 | 2.61 | 1.79 | 1.10 | 0.72 | 0.53 | 0.40 | 0.31 | 0.30 | 0.31 | 0.29 |
| $\Delta E_{2b}$ | 4.43 | 3.98 | 3.01 | 2.51 | 2.12 | 1.87 | 1.72 | 1.57 | 1.44 | 1.32 | 1.21 |

Example 3

Production of Water-Borne Base Coats a) A red-metallic water-borne base coat of the following composition was produced:
16.4 pbw of resin solids (6.5 pbw of a polyester acrylate resin, 7.3 pbw of a polyurethane resin, 2.6 pbw of hexamethoxymethylmelamine)
0.04 pbw of Printex® U from Degussa
0.9 pbw of Iriodin® 9524 from Merck
0.85 pbw of Irgazin® Rubin TR from Ciba
0.55 pbw of Quindo® Magenta RV6843 from Sun Chemical
0.05 pbw of Monolite® Blue 3R from Heubach
0.73 pbw of Paliocrom® Orange L 2800 from BASF
0.18 pbw of Xirallic® F60-51 from Merck
0.3 pbw of dimethylethanolamine
0.6 pbw of polyacrylic acid thickener
0.3 pbw of Laponite SH from Southern Clay Products
0.7 pbw of polypropylene glycol 900
14 pbw of organic solvents (6.9 pbw of ethylene glycol monobutyl ether, 1.2 pbw of ethylene glycol monohexyl ether, 1.9 pbw of N-methylpyrrolidone, 1.1 pbw of n-butanol, 1.2 pbw of n-propanol, 1.7 pbw of white spirit)
64.4 pbw of deionized water.

The red-metallic water-borne base coat had a black/white opacity of 19 μm.

b) A water-borne base coat was produced by mixing 100 pbw of the red-metallic water-borne base coat from a) with 100 pbw of the white water-borne base coat from 1a).

Example 4

Production of Multi-Layer Coatings a) A multi-layer coating was obtained by the following procedure:

The water-borne base coat 3b) was applied by electrostatically-assisted rotary spraying in a dry film thickness of 10 μm to automotive steel test panels 300 mm×600 mm in size and provided with an EDC primer and a dark-grey primer surfacer (lightness L*=14.6; colorimetrically determined at an illumination angle of 45° to the perpendicular and an observation angle of 45° relative to the specular reflection).

After flashing-off for 2 minutes at room temperature the red-metallic water-borne base coat 3a) was pneumatically spray applied in a wedge-shaped gradient (wedge in longitudinal direction) to a dry film thickness range from 0 to 10 μm and allowed to flash-off for 5 minutes at 80° C.

The test panels provided in this way with a flashed off base coat layer were then spray coated with a commercial two-component polyurethane clear coat in a dry film thickness of 40 μm and after flashing-off for 5 minutes at 20° C. baked for 20 minutes at 140° C. object temperature.

b): A multi-layer coating was produced by repeating Example 4a) with the difference that the water-borne base coat 3a) was used instead of the water-borne base coat 3b), i.e., water-borne base coat 3a) was used to apply the first 10 μm thick layer as well as the wedge-shaped layer.

c): A multi-layer coating was produced without making use of water-borne base coat 3b). To this end the red-metallic water-borne base coat 3a) was spray applied in a dry film thickness of 20 μm to an automotive steel test panel provided with the EDC primer and the dark-grey primer surfacer. To this end 2 spray passes in each case followed by a forced drying step of 5 minutes at 70° C. were performed (first spray pass: electrostatically-assisted rotary spray application in a dry film thickness of 10 μm; second spray pass: pneumatic spray application in a dry film thickness of 10 μm). Thereafter the two-component polyurethane clear coat was spray applied in a dry film thickness of 40 μm and after flashing-off for 5 minutes at 20° C. baked for 20 minutes at 140° C. object temperature.

The multi-layer coatings 4a) and 4b) so obtained were in each case colorimetrically assessed at an illumination angle of 45° to the perpendicular and at observation angles of 15, 25, 45, 75 and 110° relative to the specular reflection in accordance with the method known from U.S. Pat. No. 5,991,042 using the X-Rite MA 68 II instrument sold by the company X-Rite. Multi-layer coating 4c) was colorimetrically measured using the same equipment.

Table 2 shows the $\Delta E$ values calculated from the colorimetric data as a function of the dry film thickness of the base coat layer applied as a wedge from water-borne base coat 3a) [$\Delta E_{4a}$=square root of $(L^*_{4c}{}^2-L^*_{4a}{}^2+c^*_{4c}{}^2-c_{4a}{}^2+h^*_{4c}{}^2-h^*_{4a}{}^2)$; $\Delta E_{4b}$=square root of $(L^*_{4c}{}^2-L^*_{4b}{}^2+c^*_{4c}{}^2-c^*_{4b}{}^2+h^*_{4c}{}^2-h^*_{4b}{}^2)$].

TABLE 2

| | Dry film thickness of wedge-shaped 3a)-layer (μm) | | | | | |
|---|---|---|---|---|---|---|
| | 0 | 2 | 4 | 5 | 6 | 7 |
| $\Delta E_{4a}$ 15° | 3.97 | 2.26 | 1.32 | 0.88 | 0.90 | 0.98 |
| $\Delta E_{4a}$ 25° | 4.40 | 2.57 | 1.57 | 0.64 | 0.30 | 0.46 |
| $\Delta E_{4a}$ 45° | 4.53 | 2.64 | 1.26 | 0.54 | 0.68 | 0.93 |
| $\Delta E_{4a}$ 75° | 3.91 | 2.26 | 1.45 | 0.83 | 0.17 | 0.37 |
| $\Delta E_{4a}$ 110° | 3.67 | 2.06 | 1.31 | 0.63 | 0.24 | 0.22 |
| $\Delta E_{4b}$ 15° | 1.95 | 1.52 | 1.14 | 0.99 | 0.82 | 0.73 |
| $\Delta E_{4b}$ 25° | 2.71 | 2.12 | 1.71 | 1.22 | 0.84 | 0.81 |
| $\Delta E_{4b}$ 45° | 2.49 | 2.06 | 1.26 | 1.03 | 0.82 | 0.67 |
| $\Delta E_{4b}$ 75° | 1.14 | 0.92 | 0.88 | 0.84 | 0.94 | 1.07 |
| $\Delta E_{4b}$ 110° | 0.51 | 0.58 | 0.97 | 1.07 | 1.14 | 1.30 |

What is claimed is:

1. A process for the production of multi-layer coatings in an A' color shade on substrates, comprising the successive steps:
   1) applying a base coat layer in a total process film thickness in the range from 8 to 20 μm to substrates selected from the group consisting of metal substrates provided with a precoating comprising an external primer surfacer layer, plastics substrates provided with a plastics primer precoating and uncoated plastics substrates,
   2) applying a clear coat layer onto the base coat layer,
   3) jointly curing the base coat and clear coat layers, wherein the base coat layer is applied in a first layer and in a second layer; the first layer comprises a water-borne base coat AB and the second layer comprises a water-borne base coat A having a color shade A', wherein the water-borne base coat A is a solid color base coat having a black/white opacity of >25 μm to 80 μm or a special effect base coat having a black/white opacity of >15 μm to 80 μm, wherein the water-borne base coat AB is a mixture of 100 pbv of the water-borne base coat A and 1 to 400 pbv of a water-borne base coat B having a color shade B', wherein the water-borne base coat B is either a solid color base coat with a black/white opacity of 5 to ≤25 μm or a special effect base coat with a black/white opacity of 5 to ≤15, and wherein the pigment content of the water-borne base coat B is made such that the multi-layer coatings achieved after step 3) achieve color shade consistency from in each case at least 80% of the individual process film thickness both of the layer applied from the water-borne base coat AB and of the layer applied from the water-borne base coat A.

2. The process of claim 1, wherein at least some of the substrates have color shades which, even when overcoated with a 20 μm thick layer of the water-borne base coat A, do not allow color shade consistency to be achieved.

3. The process of claim 1, wherein all the substrates have one and the same color shade which, even when overcoated with a 20 μm thick layer of the water-borne base coat A, does not allow color shade consistency to be achieved.

4. The process of claim 1, wherein the metal substrates are selected from the group consisting of automotive bodies and automotive body parts and wherein the plastics substrates are selected from the group consisting of automotive plastics parts and automotive plastics attachments.

5. The process of claim 1, wherein the individual process film thickness of the first base coat layer of the water-borne base coat AB is in the range from 6 to 15 μm and the individual process film thickness of the second base coat layer of the water-borne base coat A is in the range from 2 to 10 μm.

6. The process of claim 1, wherein the pigment composition of the water-borne base coat B is selected from the group consisting of a pigment composition comprising 30 or more wt. % of carbon black, a pigment composition comprising 70 or more wt. % of titanium dioxide and a pigment composition comprising 40 or more wt. % of phthalocyanine pigments.

7. The process of claim 1 being performed in an industrial coating facility.

8. The process of claim 7, wherein in addition substrates are provided with multi-layer coatings in B' color shades and wherein the water-borne base coats A and the water-borne base coats B together represent the color shade program selected for the substrates to be multi-layer coated.

9. The process of claim 1, wherein formation of the water-borne base coat AB by mixing water-borne base coats A and B is performed on the paint manufacturer's premises or on the user's premises.

* * * * *